(12) United States Patent
Dolgonos et al.

(10) Patent No.: US 11,523,866 B2
(45) Date of Patent: Dec. 13, 2022

(54) MULTI-CARRIER ABLATION GENERATOR

(71) Applicant: Urocam Inc., Vaughan (CA)

(72) Inventors: Alex Dolgonos, Vaughan (CA); Karen Safaryan, Vaughan (CA)

(73) Assignee: UROCAM INC., Vaughan (CA)

( * ) Notice: Subject to any disclaimer, the term of this patent is extended or adjusted under 35 U.S.C. 154(b) by 786 days.

(21) Appl. No.: 16/275,184

(22) Filed: Feb. 13, 2019

(65) Prior Publication Data

US 2019/0247118 A1    Aug. 15, 2019

Related U.S. Application Data

(60) Provisional application No. 62/630,785, filed on Feb. 14, 2018.

(51) Int. Cl.
*A61B 18/18* (2006.01)
*A61B 18/00* (2006.01)

(52) U.S. Cl.
CPC .......... *A61B 18/1815* (2013.01); *A61B 2018/00577* (2013.01); *A61B 2018/00642* (2013.01); *A61B 2018/00702* (2013.01); *A61B 2018/00732* (2013.01); *A61B 2018/00779* (2013.01); *A61B 2018/00785* (2013.01); *A61B 2018/183* (2013.01); *A61B 2018/1823* (2013.01); *A61B 2018/1869* (2013.01); *A61B 2018/1876* (2013.01)

(58) Field of Classification Search
CPC .......... A61B 18/18; A61B 18/1815; A61B 2018/00779; A61B 2018/00785; A61B 2018/00702; A61B 2018/00732; A61B 2018/1823; A61B 2018/183; A61B 2018/1861; A61B 2018/1869; A61B 2018/1876; A61B 2018/1884; A61B 2018/1892; A61B 2018/00577; A61B 2018/00642
USPC ............ 606/33, 34, 38, 42; 607/98, 99, 101, 607/115, 116, 154–156
See application file for complete search history.

(56) References Cited

U.S. PATENT DOCUMENTS

| | | | | |
|---|---|---|---|---|
| 4,092,617 A | * | 5/1978 | Fletcher | H03H 7/24 333/17.1 |
| 5,501,704 A | * | 3/1996 | Chang | A61N 5/00 607/45 |
| 7,070,595 B2 | * | 7/2006 | Ormsby | A61B 18/1492 607/101 |
| 8,152,801 B2 | | 4/2012 | Goldberg et al. | |
| 8,647,585 B2 | * | 2/2014 | Hancock | A61L 2/24 422/186 |
| 9,007,070 B2 | | 4/2015 | Mcerlean et al. | |
| 2004/0153767 A1 | * | 8/2004 | Dolgonos | H04H 60/14 714/18 |

(Continued)

*Primary Examiner* — Thomas A Giuliani
(74) *Attorney, Agent, or Firm* — Polsinelli PC

(57) ABSTRACT

A multicarrier ablation system comprising: an antenna for application to biological tissue; a multi-carrier signal generator configured to provide a forward radio frequency (RF) signal to the antenna, the forward RF signal comprising multiple subcarriers that occupy respective frequencies within a bandwidth of the RF signal; and a monitoring circuit configured to receive a reflected RF signal from the antenna and control the multi-carrier signal generator to adjust one or more parameters of the forward RF signal during an ablation procedure based on the reflected RF signal.

17 Claims, 4 Drawing Sheets

(56) References Cited

U.S. PATENT DOCUMENTS

| | | | |
|---|---|---|---|
| 2007/0282200 A1* | 12/2007 | Johnson | G01S 13/89 600/437 |
| 2010/0087808 A1* | 4/2010 | Paulus | A61B 18/18 606/33 |
| 2012/0172954 A1* | 7/2012 | Zastrow | A61N 5/025 607/101 |
| 2012/0221002 A1 | 8/2012 | Long et al. | |
| 2013/0267943 A1* | 10/2013 | Hancock | A61B 18/1815 606/33 |

* cited by examiner

MULTI-CARRIER ABLATION GENERATOR

RELATED APPLICATIONS

This application claims priority to and benefit of U.S. Provisional Patent Application No. 62/630,785 filed Feb. 14, 2018, the contents of which are incorporated by reference.

FIELD

This disclosure relates to radio frequency (RF) ablation devices and methods.

BACKGROUND

Electrical ablation therapy has been used in medicine for the treatment of undesirable tissue, such as, for example, diseased tissue, cancer, malignant and benign tumors, masses, lesions, and other abnormal tissue growths. One type of ablation devices include radio frequency (RF) ablation devices. Some RF ablation devices generate continuous wave (CW) radio signals at different frequencies (for example, in the UHF/S band) at specified output power for application to biological tissue.

Improved RF ablation devices and methods are desired.

SUMMARY

According to a first example aspect is a multicarrier ablation system that includes an antenna for application to biological tissue, a multi-carrier signal generator configured to provide a forward radio frequency (RF) signal to the antenna, the forward RF signal comprising multiple subcarriers that occupy respective frequencies within a bandwidth of the RF signal, and a monitoring circuit configured to receive a reflected RF signal from the antenna and control the multi-carrier signal generator to adjust one or more parameters of the forward RF signal during an ablation procedure based on the reflected RF signal.

In some example embodiments, the multiple subcarriers are orthogonal frequency division multiplexed (OFDM) subcarriers. In some examples embodiments, the forward RF signal is a continuous wave microwave signal. In some examples, the forward RF signal is within the 915 MHz band or the 2.4 GHz band.

In some example embodiments, the monitoring circuit is configured to receive a portion of the forward RF signal and perform a comparison of the subcarriers of the forward RF signal with corresponding subcarriers of the reflected RF signal.

In some example embodiments, the parameters include one or both of a phase and an amplitude of the individual subcarriers that comprise the forward RF signal. In some example embodiments, the parameters include one or more of a power of the forward RF signal, a bandwidth of the forward RF signal, a number of the subcarriers, and a frequency spacing of the subcarriers. In some example embodiments, the power is between 100 W and 200 W; the bandwidth of the forward RF signal is between 8 MHz and 50 MHzm and the number of subcarriers is between 100 to 4000.

In some example embodiments, the monitoring circuit is configured to adjust an amplitude of one or more of the subcarriers to mitigate against hotspots occurring in an RF signal transmission path of the system. In some example embodiments, the monitoring circuit is configured to cause the multi-carrier signal generator to maintain a constant average power across the bandwidth of the forward RF signal during the ablation procedure.

In some example embodiments, the multi-carrier signal generator is configured to perform an inverse fast Fourier transform on multiple signals to provide the forward RF signal, and the monitoring circuit is configured to perform a fast Fourier transform on at least the reflected RF signal.

In some example embodiments, the monitoring circuit is configured to cause the multi-carrier signal generator to remove subcarriers from the forward RF signal to mitigate notches that would otherwise result from changes in a voltage standing wave ratio (VSWR) in the antenna.

In some example embodiments, the monitoring circuit is configured to cause the multi-carrier signal generator to sweep at least some of the subcarriers by changing one or more of a phase and amplitude of the subcarriers during the ablation procedure.

In some example embodiments, the monitoring circuit is configured to cause the multi-carrier signal generator to vary a frequency spacing of the subcarriers during the ablation procedure.

In some example embodiments, there is provided a method of controlling ablation system that includes an antenna for application to biological tissue, comprising: providing a forward radio frequency (RF) signal to the antenna, the forward RF signal comprising multiple subcarriers that occupy respective frequencies within a bandwidth of the RF signal; and receiving a reflected RF signal from the antenna and adjusting one or more parameters of the forward RF signal during an ablation procedure based on the reflected RF signal.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Conventional CW (Continuous Wave) tissue ablation generators apply a forward RF signal having at a specified power (for example 100W) in a defined frequency band (for example a 915 MHz band or a 2.45 GHz band) along a guided RF signal path to an antenna positioned at a target tissue. Impedance mismatch between the antenna and target tissue can cause RF power to be reflected back into the RF signal path. Performance of an ablation device can be monitored by measuring RF power reflected in the RF signal path. Interaction between the forward and reflected RF waves can produce standing waves in the RF path that varies sinusoidally in amplitude with distance from the antenna end. The ratio of the voltage maximum (antinode) to the adjacent voltage minimum (node) on the conductive RF signal path is relative to the proportion of energy reflected and the energy delivered and is called the voltage standing wave ratio (VSWR).

During an ablation process, the impedance of the target tissue can change as a result of the ablation, causing an increase in the reflected power, resulting in a higher VSWR. Among other things, this increased VSWR can introduce measurement errors and cause overheating of the RF path at the location of antinodes. VSWR and the location of the antinode hotspots (also referred to as notches) on the conductive path are a function of phase and frequency of the forward and reflected RF signals.

Example embodiments are described below that allow the RF power applied through the electrode of an ablation device to be controlled on a frequency specific basis within an applied frequency bandwidth.

As generally used herein, the terms "proximal" and "distal" generally refer to a clinician manipulating one end of an electrical ablation device to apply a signal to target tissue of a patient. The term "proximal" generally refers to the portion of the instrument closest to the clinician. The term "distal" generally refers to the portion located furthest from the clinician. In certain embodiments, electrical ablation devices may generally comprise one or more electrodes or antennas configured to be positioned into or proximal to undesirable tissue in a tissue treatment region (e.g., a target site or a worksite). The tissue treatment region may have evidence of abnormal tissue growth. In general, the antenna will comprise an electrically conductive portion (e.g., medical grade stainless steel, gold plated, etc.) that is configured to electrically couple with an energy source. Once the antenna is positioned into or proximal to the target tissue, a forward RF signal is applied to the antenna to create an electric field to which the undesirable target tissue is exposed. The energizing potential (and the resulting electric field) may be characterized by various parameters, such as, for example, frequency, and amplitude, and/or polarity.

Figure 1:
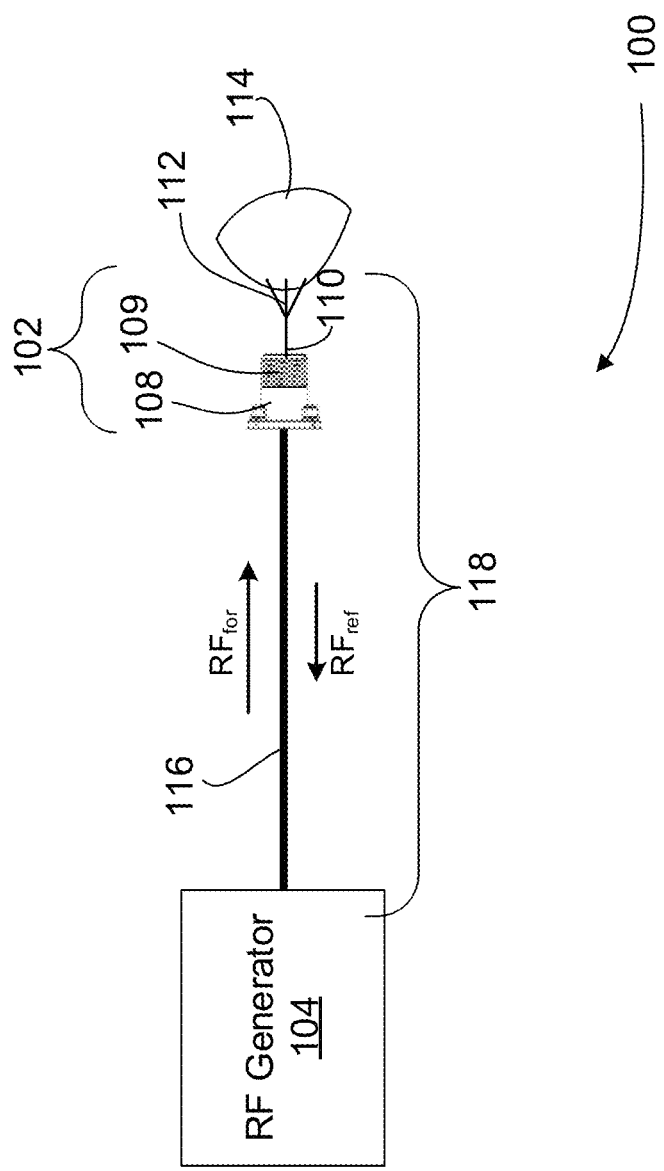
FIG. 1 is a schematic of an RF ablation system according to example embodiment.

An RF medical ablation system 100 is shown in FIG. 1, according to an example embodiment. The medical ablation system 100 generally includes an ablation probe 102 for introduction into the body of a patient for ablative treatment of target tissue, and an RF generator 104 configured for generating and providing forward RF signals ($RF_{for}$) to the ablation probe 102 through a cable 116 and receiving reflected signals ($RF_{ref}$) via the cable 116 from the ablation probe 102. The probe 102 includes a coaxial cable 108 that is electrically coupled to cable 116 (which may also be a coaxial cable). Coaxial cable 108 has an insulated conductive sheath 109 and a central conductor 110. Conductor 110 extends from a distal end of coaxial cable 108, and forms or couples with a needle antenna 112. Antenna 112 is used to apply CW RF signals at selected frequencies and a specified output power to a target biological tissue 114. The probe 102 may be rigid, semi-rigid, or flexible depending upon the designed means for introducing the needle antenna 112 to the target tissue. Ablation probe 102 may include additional components beyond what is illustrated in the simplified view of FIG. 1, including for example a handle at proximal end of the probe 102. The cable 116, coaxial cable 108 and antenna 112 collectively form a guided conductive RF signal path 118 that extends from an RF signal source within the RF generator 104 to the target tissue 114.

Figure 2:
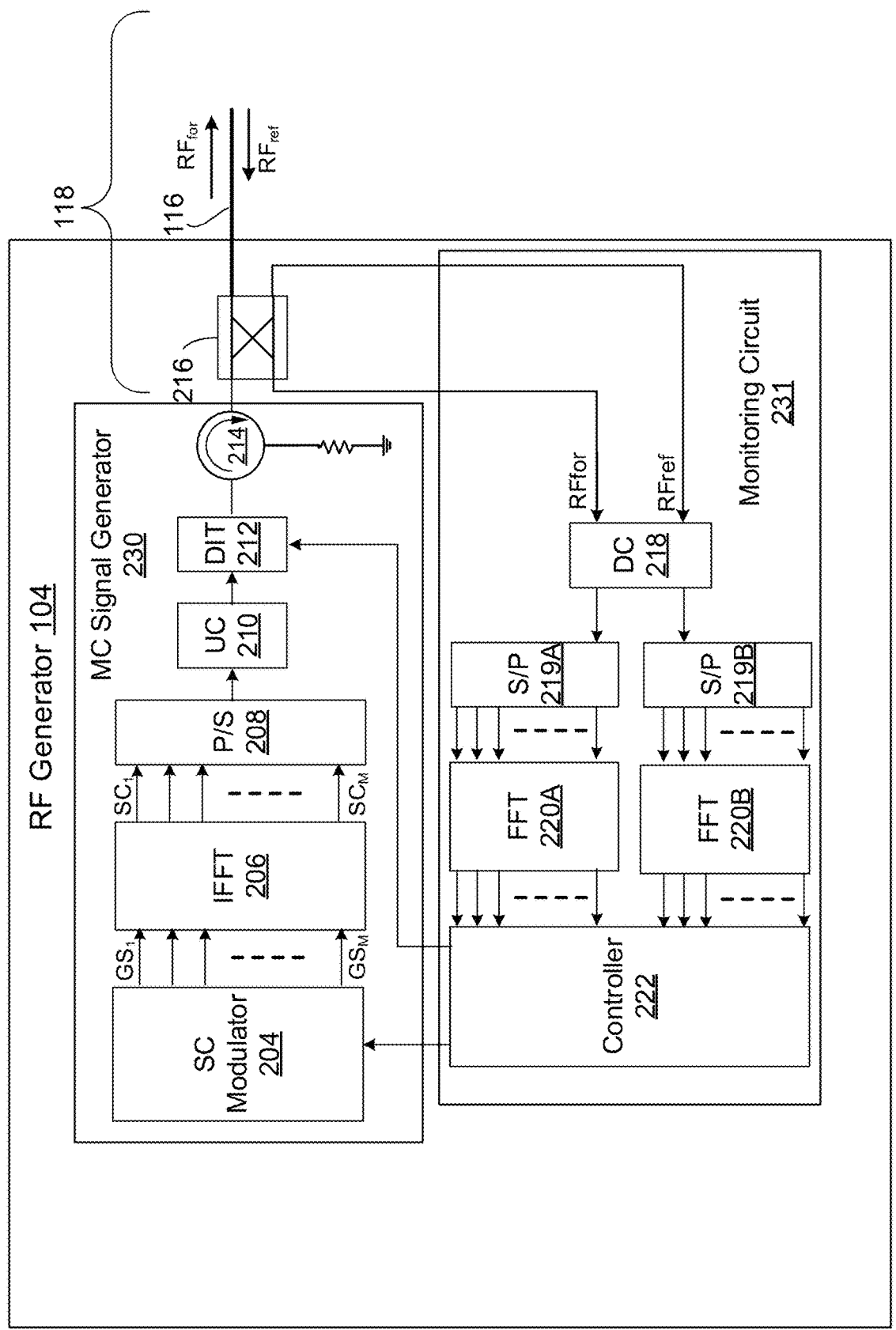
FIG. 2 is a schematic of signal generator of the RF ablation system of FIG. 1, according to an example embodiment.

A schematic of RF generator 104 is shown in FIG. 2 according to an example embodiment. RF generator 104 may be implemented using a combination of active and passive electronic components. Active components can include, among other things, one or more suitably programmed or configured digital signal processing (DSPs). As noted above, RF generator 104 provides forward RF signals $RF_{for}$ to the ablation probe 102 through a cable 116 and receives reflected signals $RF_{ref}$ through the cable 116. In this regard, RF generator 104 includes a multicarrier (MC) signal generator 230 for generating forward signals $RF_{for}$, and a signal processor 230 for receiving and processing reflected signals $RF_{ref}$. In an example embodiment, a passive four port directional coupler 216 couples the generated forward signal $RF_{for}$ output of MC signal generator 230 to cable 116. Coupler 216 is configured to substantially direct all the power of reflected signals $RF_{ref}$ on cable 116 to the monitoring circuit 231 and also to divert a small portion of the power of forward signals $RF_{for}$ to the monitoring circuit 231. In an example embodiment, coupler 216 may be a 20 dB coupler, with an insertion loss (IL) of 0.15 dB.

In an example embodiment, MC signal generator 230 is an orthogonal frequency division multiplexing (OFDM) signal generator 230 that generates an OFDM forward signal $RF_{for}$ having a bandwidth BW that include M multiple narrow-band orthogonal sub-carriers upconverted to a carrier frequency $F_c$. As will be described in greater detail below, in example embodiments, MC signal generator 230 can be controlled by monitoring circuit 231 to control the cumulative power applied across the entire bandwidth BW, to adjust a phase and amplitude of each of the M subcarriers within the bandwidth BW, and to block one or more of the M subcarriers within the bandwidth BW.

In this regard, in the illustrated embodiment, MC signal generator 230 includes an SC modulator 204 to output M generated signals $GS_1$ to $GS_M$ (individually, GSi, where $1 \le i \le M$). In an example embodiment, SC modulator 204 is controlled by signals from monitoring circuit 231 to uniquely adjust the amplitude of each generated signal GSi. In some examples, SC generator 204 is configured to also uniquely adjust the phase of each generated signal GSi. Thus, the SC modulator 204 can be controlled to specify a unique phase modulation and/or amplitude modulation for each of the signals GSi. This may for example be used to adjust the amplitude of individual signals GSi or groups of signals to zero, and at the same time raise the amplitude of other signals to maintain a constant power output over the entire group of M generated signals $GS_1$ to $GS_M$. An inverse fast Fourier transform (IFFT) 206 is applied to modulate the signals $GS_1$ to $GS_M$ onto orthogonal subcarriers $SC_1$ to $SC_M$ (individually SCi, where $1 \le i \le M$), which are combined into a single OFDM signal by a parallel to serial converter 208. The baseband OFDM signal is then modulated onto a treatment carrier frequency $F_c$ at upconverter 210. The upconverted OFDM signal can be further shaped at a digital impedance tuner (DIT) 212 that is also controlled by monitoring circuit 231.

The resulting upconverted OFDM signal output from the DIT 212 is the forward signal $RF_{for}$, which is applied to cable 116 through coupler 216. A circulator 214 may be included at the output of the MC signal generator 230 to isolate the MC signal generator 230 from reflected signals $RF_{ref}$ that are not blocked by coupler 216.

Figure 4:
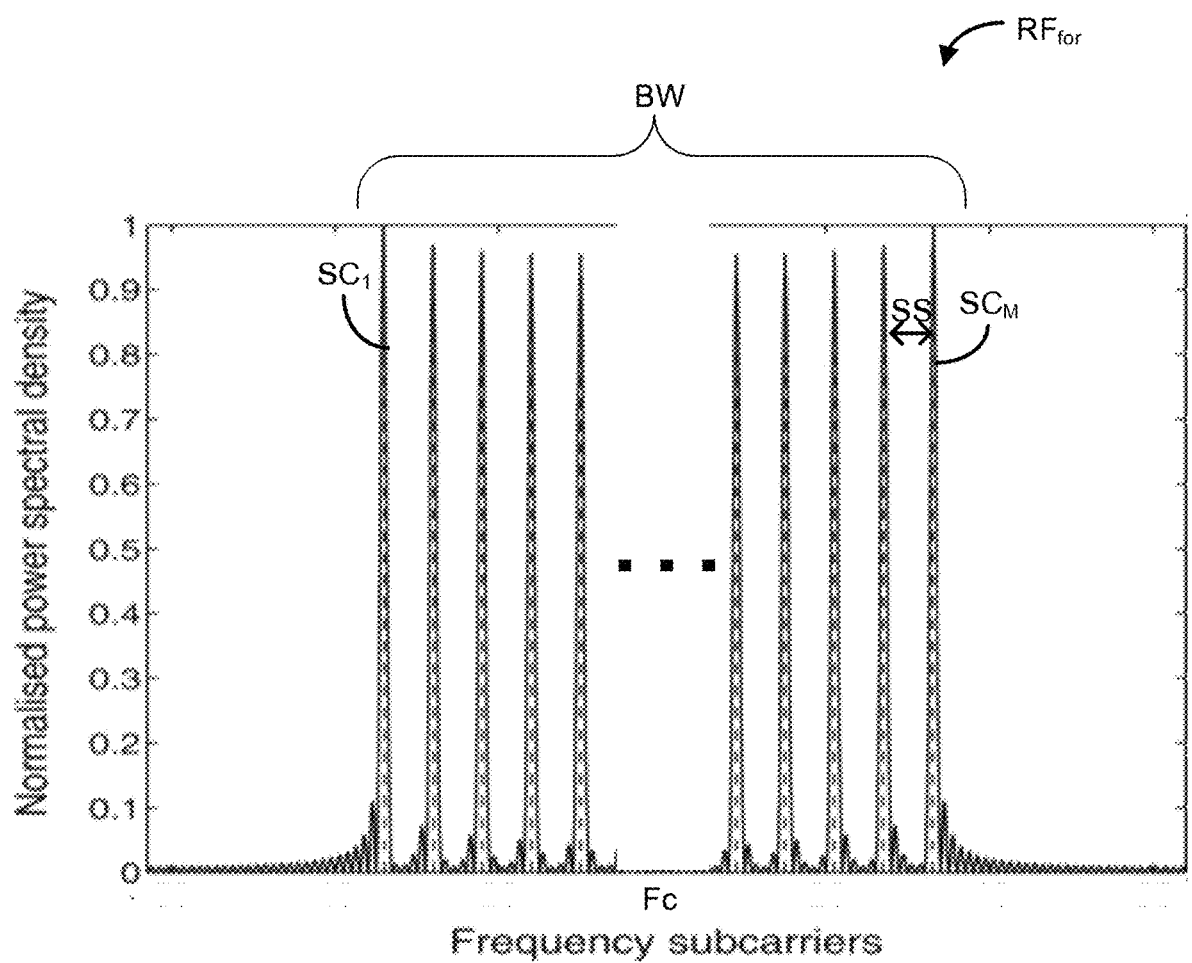
FIG. 4 is a spectral diagram of a multicarrier signal for use in the RF ablation system of FIG. 1.

An example of a signal $RF_{for}$ output by MC signal generator 230 is shown FIG. 4. In particular, in example embodiments, MC signal generator 230 configured to output a multicarrier OFDM RF signal $RF_{for}$ that has a specified power (P) within a specified bandwidth (BW) centered around a specified carrier frequency (Fc). The signal $RF_{for}$ includes a specified number (M) of subcarriers $SC_1$ to $SC_M$ having a specified inter-subcarrier frequency spacing (SS) and subcarrier frequency ($F_{sc}$). Additionally, each of the individual subcarriers $SC_1$ to $SC_M$ will have a respective amplitude (SCA(i)) and phase (SCP(i)), where i=1 to M.

As noted above Monitoring circuit 231 is configured to receive a small portion of the power of forward signal $RF_{for}$ and a substantial portion of the power of reflected signal $RE_{ref}$ from the coupler 216. Monitoring circuit 231 includes a downconverter 218 to downconvert the forward signal $RF_{for}$ and reflected signal $RE_{ref}$ to respective baseband signals, which are each converted into M parallel signals at respective serial to parallel converters 219A and 219B. Respective fast Fourier transforms 220A, 220B are applied to the parallel signals, and the resulting recovered M forward sub-carrier signals $RF_{for}$ and M reflected subcarrier signals $RE_{ref}$ are provided to a controller 222. Controller 22 is configured to analyze and compare a phase and amplitude of each of the M sub-carrier signals that make up the $RF_{for}$ and M reflected subcarrier signals $RE_{ref}$ and determine the VSWR for each of the individual subcarriers $SC_1$ to $SC_M$. Based on this information, the impedance mismatch at the treatment site of tissue 114 can be monitored in real time during an ablation procedure, and the operation of RF generator 104 modified to optimize the ablation procedure. In example embodiments, controller 222 is configured to control the SC modulator 204 and DIT 212 to accomplish one or more of the following: (1) suppress selected sub-carriers SCi within the bandwidth BW that are associated with hot-spots or notches along the RF conductive path 118, and then increase the amplitude of remaining sub-carriers SCi to maintain a constant average power (P) across the bandwidth BW; (2) monitor and control in real-time impedance mismatch occurring at the ablation site of tissue 114; (3) monitor and control the power in forward and reflected signals $RF_{for}$, $RF_{ref}$; and (4) sweep (e.g. continually modify) one or more of the subcarrier spacing SS, individual subcarrier phases SCP(i), and individual subcarrier amplitudes SCAP(i) within the bandwidth BW to mitigate against the occurrence of hotspots/notches in the conductive path, while maintaining a constant average power P across the bandwidth (BW).

Figure 3:
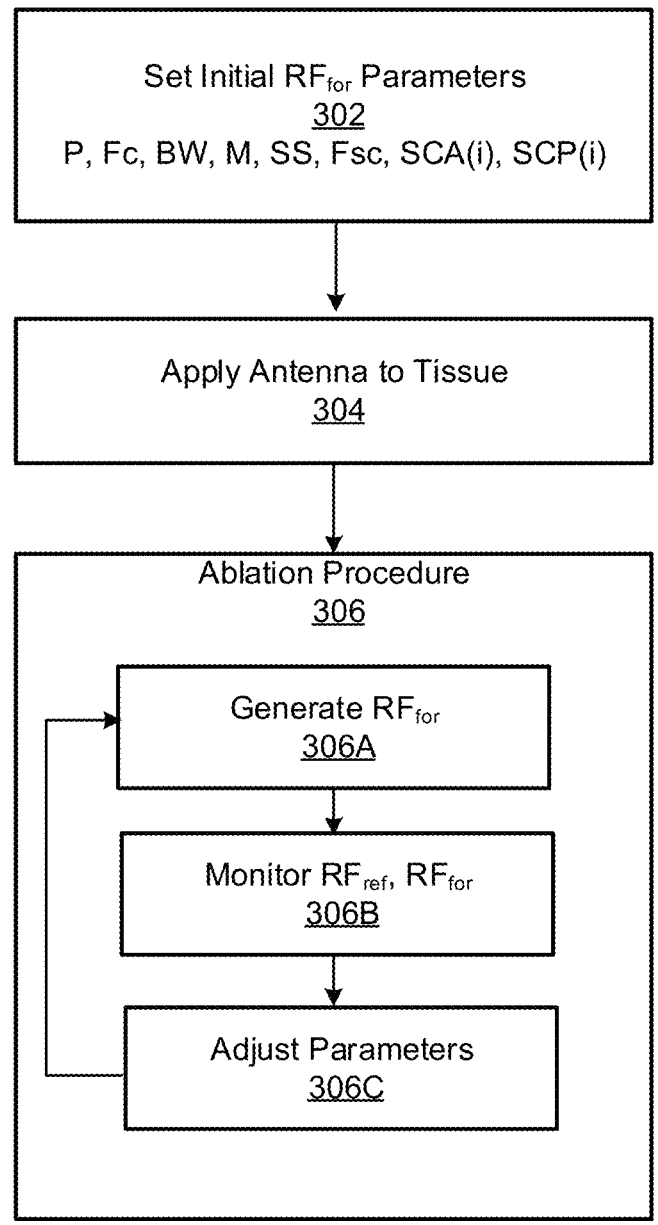
FIG. 3 is a block diagram showing a method of operation of the RF ablation system of FIG. 1.

FIG. 3 illustrates a method performed by RF ablation system 100 according to an example embodiment. Initial parameters (which could for example be preconfigured during factory configuration or specified by a clinician during setup of the RF ablation system 100) are provided for the forward signal $RF_{for}$, as indicated in step 302. These parameters can include: power (P), bandwidth (BW), a carrier frequency (Fc), number (M) of subcarriers $SC_1$ to $SC_M$, inter-subcarrier frequency spacing (SS) and subcarrier frequency ($F_{sc}$), and amplitude (SCA(i)) and phase (SCP(i)), where i=1 to M, for each of the subcarriers. In example embodiments the carrier frequency Fc is a CW microwave frequency, for example a frequency within the unlicensed 915 MHz or 2.4 GHz bands. Although many different parameter settings are possible, in some non-limiting examples, the power P, which represents an average power across the bandwidth BW, may be a specified value between 100 W and 200 W; the bandwidth BW may be between 8 MHz and 50 MHz; the number (M) of subcarriers can be 100 to 4000, and the subcarrier spacing and frequency selected to provide orthogonal subcarriers for the M subcarriers within the bandwidth BW. The amplitude and phase SCA(i) and phase SCP(i) of each of the subcarriers may be initially be set as consistent across the M sub-carriers, or may be staggered according to a predetermined pattern, to achieve the specified average power P.

As indicated at step 304, the ablation antenna 112 is applied to the target tissue 114, and the ablation procedure 306 can then be commenced. Ablation procedure 306 includes three steps 306A, 306B and 306B that continue for the duration of the procedure. In particular, as indicated in step 306A, MC signal generator 230 generates ablation forward signal $RF_{for}$ for application to the tissue 114 in accordance with the specified parameters (power P, bandwidth BW, carrier frequency Fc, number M of subcarriers $SC_1$ to $SC_M$, inter-subcarrier frequency spacing SS and subcarrier frequency $F_{sc}$, and individual subcarrier amplitude SCA(i) and phase SCP(i)). As indicated in step 306B, while forward signal $RF_{for}$ is being applied to the tissue 114, monitoring circuit 231 monitors both the forward signal $RF_{for}$ and the reflected signal $RF_{rev}$ to determine in real-time VSWR, impedance mismatch, and potential notches/hotspot locations. As indicated in step 306C, the controller 222 of monitoring circuit 231 then calculates and adjusts the parameters used by the MC signal generator 230 to generate ablation forward signal $RF_{for}$.

Among other things, the ablation procedure 306 enables the multi-carrier OFDM RF signal $RF_{for}$, to be adjusted to achieve one or more of the following: (1) removal of the subcarriers associated with RF notches that would otherwise be created in the conductive path 118 due to increased VSWR; (2) accurate measurement and control of forward and reflected power; (3) monitoring and control in real-time of the impedance mismatch between radiating antenna 112 and tissue 114, during the ablation procedure; (4) creation of a desired influential pattern to biological processes across the bandwidth BW inside the tissue by using a variety of amplitude (AM) and phase (PM) modulation for each subcarrier $SC_i$.

Thus, as described above, the multi-carrier forward signal $RF_{for}$ is composed using an inverse Fourier transform. This allows creating an CW RF signal with a specified number of subcarriers, bandwidth, frequency separation between subcarriers and individual AM and PM modulation for every subcarrier inside the spectrum BW. During the ablation procedure the reflected power of the reflected multi-carrier signal is analyzed using a direct Fourier transform, allowing the frequencies that, due to impedance mismatch, lead to the creation of RF notches. Additionally, the RF power and phase shift between forward and reflected signals can be monitored. The value and sign of the phase shift provides information pertaining to the magnitude and type impedance mismatch (inductive or capacitive) during ablation of tissue. In example embodiments, based on the monitored signals, the MC generator 230 can be controlled to remove, shift or sweep the power and phase of the subcarriers that are associated with notches, but also keep the radiated to tissue RF power at constant level by one or more of the following actions: (1) remove the carriers inside the bandwidth BW at the frequency band or bands that are associated with the notch or notches, and recalculate and adjust the required power (amplitude) of the remaining carries to keep a consistent average RF power level applied to tissue after removing the subcarriers; (2) shifting or sweeping the phase of individual subcarriers; (3) sweeping subcarrier spacing; and (4) detect the frequencies of notches and switch power to subcarriers out of the notch frequency.

In addition to mitigating against notches that result in hotspots in the conductive path 110, accurate measurement and control of the forward and reflected signals $RF_{for}$, $RF_{ref}$ can mitigate against impedance mismatch that would otherwise vary over the ablation procedure. Among other things, this can allow a consistent and controlled amount of power to be applied throughout the ablation procedure.

Using a multi-carrier OFDM waveform for tissue ablation can address a number of the problems of known CW systems. In at least some applications, the system described herein may significantly decrease or even eliminate power reflected back from the tissue. In some cases, when reflected power can not be totally eliminated, the described system allows the anti-nodes of standing waves to be shifted along the conductive RF path 118, providing an evenly distributed temperature profile along the RF path 118 to eliminate over-heated points/zones. In at least some examples, a multi-carrier OFDM signal is formed by a synthesized waveform composed by an IFFT using DSP. This allows creation of a signal with a wideband RF spectrum, with multiple orthogonal subcarriers. The number of subcarriers and spacing between the subcarriers inside the generated spectrum BW can be controlled. The RF power of the multi-carrier OFDM signal is applied into tissue 114 and the signal reflected back from the tissue is analyzed, together with the forward signal, as multi-carrier OFDM signals by applying an FTT using DSP to the forward and reflected signals. Accurate measurements can be made of the amplitudes, phases and impedance mismatch for all reflected back subcarriers, as well as for forward carriers. This enables accurate measurement of both forward and reflected power and calculation of the exact value of RF energy absorbed into tissue 114.

Certain adaptations and modifications of the described embodiments can be made. Therefore, the above discussed embodiments are considered to be illustrative and not restrictive.

What is claimed is:

1. A multi-carrier ablation system comprising:
an antenna for application to biological tissue;
a multi-carrier signal generator configured to provide a forward radio frequency (RF) signal to the antenna, the forward RF signal comprising multiple generated signals, the multiple generated signals being modulated onto respective subcarriers that occupy respective frequencies within a bandwidth of the forward RF signal, the subcarriers being orthogonal frequency division multiplexed (OFDM) subcarriers; and
a monitoring circuit configured to receive a reflected RF signal from the antenna and a portion of the forward RF signal from the multi-carrier signal generator, the monitoring circuit being configured to perform a comparison of a phase and an amplitude of each of the multiple subcarrier signals of the forward RF signal with a phase and an amplitude of corresponding subcarrier signals of the reflected RF signal and control the multi-carrier signal generator to adjust one or more parameters of the forward RF signal during an ablation procedure based on the comparison.

2. The system of claim 1 wherein the forward RF signal is a continuous wave microwave signal.

3. The system of claim 1 wherein the forward RF signal is within the 915 MHz band or the 2.4 GHz band.

4. The system of claim 1 wherein the parameters include one or both of the phase and the amplitude of the individual subcarriers that comprise the forward RF signal.

5. The system of claim 1 wherein the parameters include one or more of a power of the forward RF signal, the bandwidth of the forward RF signal, a number of the subcarriers, and a frequency spacing of the subcarriers.

6. The system of claim 5 wherein the power is between 100 W and 200 W; the bandwidth of the forward RF signal is between 8 MHz and 50 Mhz and the number of subcarriers is between 100 to 4000.

7. The system of claim 1 wherein the parameters include a power of the forward RF signal, the bandwidth of the forward RF signal, a number of the subcarriers, and a frequency spacing of the subcarriers, wherein the power is between 100 W and 200 W; the bandwidth of the forward RF signal is between 8 MHz and 50 Mhz and the number of subcarriers is between 100 to 4000.

8. The system of claim 1 wherein the monitoring circuit is configured to adjust the amplitude of one or more of the subcarriers to mitigate against hotspots occurring in an RF signal transmission path of the system.

9. The system of claim 1 wherein the monitoring circuit is configured to cause the multi-carrier signal generator to maintain a constant average power across the bandwidth of the forward RF signal during the ablation procedure.

10. The system of claim 1 wherein the multi-carrier signal generator is configured to perform an inverse fast Fourier transform on multiple signals to provide the forward RF signal, and the monitoring circuit is configured to perform a fast Fourier transform on at least the reflected RF signal.

11. The system of claim 1 wherein the monitoring circuit is configured to cause the multi-carrier signal generator to remove subcarriers from the forward RF signal to mitigate notches that would otherwise result from changes in a voltage standing wave ratio (VSWR) in the antenna.

12. The system of claim 11, wherein the monitoring circuit is configured to cause the multi-signal generator to remove subcarriers by suppressing selected subcarriers within the forward RF signal.

13. The system of claim 12, wherein in response to suppressing the one or more selected subcarriers within the bandwidth, the monitoring circuit is configured to cause the multi-carrier signal generator to increase the amplitude of remaining subcarriers to maintain a constant average power across the bandwidth of the forward RF signal.

14. The system of claim 1 wherein the monitoring circuit is configured to cause the multi-carrier signal generator to sweep at least some of the subcarriers by changing one or more of the phase or the amplitude of the subcarriers during the ablation procedure.

15. The system of claim 14, wherein the monitoring circuit is configured to cause the multi-carrier signal generator to maintain a constant average power across the bandwidth of the forward RF signal when sweeping the at least some of the subcarriers.

16. The system of claim 1 wherein the monitoring circuit is configured to cause the multi-carrier signal generator to vary a frequency spacing of the subcarriers during the ablation procedure.

17. The system of claim 1, wherein the monitoring circuit is configured to analyze the phase and the amplitude of each of the multiple subcarrier signals of the forward RF signal and the reflected RF signal to determine a voltage standing wave ratio (VSWR) for each of the individual subcarriers.

* * * * *